(12) United States Patent
Yamada et al.

(10) Patent No.: US 10,702,297 B2
(45) Date of Patent: Jul. 7, 2020

(54) ULTRASONIC TREATMENT INSTRUMENT FOR ARTICULATIONS, AND TREATMENT METHOD THEREOF

(71) Applicant: OLYMPUS CORPORATION, Hachioji-shi, Tokyo (JP)

(72) Inventors: Masashi Yamada, Sagamihara (JP); Yasuo Tanigami, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 116 days.

(21) Appl. No.: 16/145,854

(22) Filed: Sep. 28, 2018

(65) Prior Publication Data

US 2019/0029708 A1 Jan. 31, 2019

Related U.S. Application Data

(63) Continuation of application No. PCT/JP2016/059912, filed on Mar. 28, 2016.

(51) Int. Cl.
*A61B 17/32* (2006.01)
*A61B 17/16* (2006.01)
*A61B 17/00* (2006.01)

(52) U.S. Cl.
CPC .. *A61B 17/320068* (2013.01); *A61B 17/1659* (2013.01); *A61B 17/1626* (2013.01); *A61B 2017/00017* (2013.01); *A61B 2017/00084* (2013.01); *A61B 2017/00831* (2013.01); *A61B 2017/00964* (2013.01); *A61B 2017/00973* (2013.01); *A61B 2017/320072* (2013.01); *A61B 2017/320082* (2017.08); *A61B 2017/320088* (2013.01)

(58) Field of Classification Search
CPC ............... A61B 17/320068; A61B 17/1659
See application file for complete search history.

(56) References Cited

U.S. PATENT DOCUMENTS

| 2,714,890 | A | * | 8/1955 | Vang | A61B 17/320068 |
| | | | | | 606/169 |
| 5,188,102 | A | * | 2/1993 | Idemoto | A61B 17/320068 |
| | | | | | 604/22 |
| 6,423,082 | B1 | * | 7/2002 | Houser | A61B 17/320068 |
| | | | | | 606/169 |

(Continued)

FOREIGN PATENT DOCUMENTS

| EP | 2135569 A2 | 12/2009 |
| JP | 2003-126110 A | 5/2003 |

(Continued)

OTHER PUBLICATIONS

Jul. 2, 2019 Office Action issued in Japanese Patent Application No. 2018-507839.

(Continued)

*Primary Examiner* — Christian A Sevilla
(74) *Attorney, Agent, or Firm* — Oliff PLC (57) ABSTRACT

The treatment section integrally includes, on the distal side of a probe, a cortical bone abrasion portion which abrades a living body tissue or a bone among treated target parts by mechanical abrasion by ultrasonic vibration, and a cartilage abrasion portion which generates heat by ultrasonic vibration and abrades a cartilage among the treated target parts by dissolutive abrasion.

9 Claims, 6 Drawing Sheets

(56) References Cited

U.S. PATENT DOCUMENTS

| | | | | |
|---|---|---|---|---|
| 6,562,032 B1* | 5/2003 | Ellman | .......... | A61B 17/320068 |
| | | | | 606/41 |
| 7,476,233 B1* | 1/2009 | Wiener | .......... | A61B 17/320068 |
| | | | | 606/169 |
| 2002/0077645 A1* | 6/2002 | Wiener | .......... | A61B 17/320068 |
| | | | | 606/169 |
| 2003/0073987 A1 | 4/2003 | Sakurai et al. | | |
| 2006/0195106 A1 | 8/2006 | Jones et al. | | |
| 2006/0211943 A1* | 9/2006 | Beaupre | ......... | A61B 17/320068 |
| | | | | 600/471 |
| 2008/0234710 A1* | 9/2008 | Neurohr | ......... | A61B 17/320068 |
| | | | | 606/169 |
| 2009/0318944 A1 | 12/2009 | Kimura et al. | | |

FOREIGN PATENT DOCUMENTS

| | | |
|---|---|---|
| JP | 2008-528242 A | 7/2008 |
| JP | 2015-43879 A | 3/2015 |
| JP | 2015-128628 A | 7/2015 |

OTHER PUBLICATIONS

Jun. 21, 2016 International Search Report issued in International Patent Application No. PCT/JP2016/059912.

\* cited by examiner

ULTRASONIC TREATMENT INSTRUMENT FOR ARTICULATIONS, AND TREATMENT METHOD THEREOF

CROSS-REFERENCE TO RELATED APPLICATIONS

This is a Continuation Application of PCT Application No. PCT/JP2016/059912, filed Mar. 28, 2016, the entire contents of which are incorporated herein by references.

BACKGROUND OF THE INVENTION

1. Field of the Invention

The present invention relates to an ultrasonic treatment instrument for articulations, which has both a mechanical abrasion function by ultrasonic vibration and a dissolutive abrasion function by heat, and a treatment method thereof.

2. Description of the Related Art

In general, a cartilage is formed of protein (collagen) as a main component, and is soft and elastic. Abrasion of a cartilage in a surgical treatment is performed by using a treatment instrument such as an electric scalpel. In addition, in recent years, it has been reported that, with use of an ultrasonic treatment instrument, a surgical treatment such as abrasion can be performed not only on a living body tissue, but also on a treated target part such as a bone. Normally, it is assumed that even if vibration is applied to a cartilage, the vibration is absorbed in the cartilage by elastic force, and it is thought that a mechanical abrasion function by ultrasonic vibration does not occur.

For example, if an ultrasonic treatment instrument, which generates ultrasonic vibration along with heat generation, as disclosed in Jpn. Pat. Appln. KOKAI Publication No. 2015-43879 (patent document 1), is used, an abrasion treatment can be performed on all parts of bones (cortical bones and cancellous bones), such as a cartilage and a subcartilaginous bone, and living body tissues. On the other hand, since the abrasion treatment can be performed on all parts, it is not easy to realize an abrasion treatment for cutting apart a living body tissue and a cartilage, and cutting apart a cartilage and a subcartilaginous bone. For example, in a surgery of articulations, it is necessary to cut apart a cartilage, a synovium and a subcartilaginous bone. In a cutting-and-opening treatment and an abrasion treatment, it is important for a surgeon to ascertain cutting and dividing of parts so that an underlying part may not be damaged as much as possible, and the surgeon is required to have experience and skill.

The present invention provides an ultrasonic treatment instrument for articulations, and a treatment method thereof, the ultrasonic treatment instrument for articulations including a treatment section which includes both a bone abrasion portion which abrades a living body tissue or a bone that is a treated target part by mechanical abrasion by ultrasonic vibration, and a cartilage abrasion portion which dissolves and abrades a cartilage of a treated target part by generating heat by ultrasonic vibration.

BRIEF SUMMARY OF THE INVENTION

According to an embodiment of the present invention, there is provided an ultrasonic treatment instrument for articulations, comprising: an ultrasonic vibration generator configured to generate ultrasonic vibration; an ultrasonic probe configured to transmit the ultrasonic vibration; and a treatment section provided at a distal end of the ultrasonic probe and configured to perform a desired treatment on a treated target part, the treatment section comprising: a bone abrasion portion configured to come in contact with a living body tissue or a bone of the treated target part by a surface having an edge, and to configured to mechanically abrade the living body tissue or the bone by beating the living body tissue or the bone by the transmission of the ultrasonic vibration; and a cartilage abrasion portion provided at a different position from, or at an identical overlapping position to, a position of the bone abrasion portion, configured to come in contact with a cartilage of the treated target part, and configured to generate heat by the transmission of the ultrasonic vibration and to dissolutively abrade the cartilage.

Furthermore, according to an embodiment of the present invention, there is provided a treatment method of an ultrasonic treatment instrument for articulations, the treatment method being a method of abrading a treated target part by the ultrasonic treatment instrument for articulations of claim 1, the treatment method comprising: generating ultrasonic vibration by an ultrasonic vibration generator, and transmitting the ultrasonic vibration to an ultrasonic probe; causing a bone abrasion portion, which a treatment section provided at a distal end of the ultrasonic probe includes, to come in contact with a living body tissue or a bone of the treated target part by a surface having an edge, and causing the bone abrasion portion to mechanically abrade the living body tissue or the bone by beating the living body tissue or the bone by the transmission of the ultrasonic vibration; and causing a cartilage abrasion portion, which the treatment section provided at the distal end of the ultrasonic probe includes and which is provided at a different position from, or at an identical overlapping position to, a position of the bone abrasion portion, to come in contact with a cartilage of the treated target part, and causing the cartilage abrasion portion to generate heat by the transmission of the ultrasonic vibration and to dissolutively abrade the cartilage.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be described in detail with reference to the accompanying drawings.

An ultrasonic treatment instrument for articulations of the present embodiment can perform a surgical treatment on a desired treated target part by ultrasonic vibration. The ultrasonic treatment instrument for articulations includes a treatment section. The term "mechanical abrasion" here means beating and crushing a treated target part by ultrasonic vibration. In the description below, the mechanical abrasion is referred to as "mechanical abrasion" or "crushing abrasion". Besides, in some cases, since the mechanical abrasion means that the probe beats the treated target part by swinging due to the amplitude of ultrasonic vibration, the mechanical abrasion is also referred to as "hammering effect" or "hammering function".

The abrasion on a cartilage by the cartilage abrasion portion occurs by the cartilage abrasion portion being pushed on the cartilage, and by locally heating the cartilage up to a temperature at which the cartilage is dissolved. In a first embodiment, for example, the cartilage abrasion portion of the treatment section generates heat by internal friction of a probe 7 at a time when ultrasonic vibration is applied. Alternatively, in a second embodiment, the cartilage abrasion portion of the treatment section generates heat by residual stress (to be described later). Thereby, the temperature of the cartilage is raised up to a proper temperature at which the cartilage can be dissolved. As the proper temperature, the temperature of the cartilage abrasion portion is set such that the temperature of the cartilage part of the treated target, which is put in contact, rises up to a range of 45° C. to 220° C., more preferably 120° C. to 160° C. The heat generation by internal friction of the probe can be caused by the incorporation of a metallic material which has greater damping or damping capacity than a titanium alloy or the like, the metallic material being added to the cartilage abrasion portion that is formed of a titanium alloy or the like. In the case of this configuration, heat generation depends on the inherent characteristics of the incorporated metallic material (e.g. the logarithmic decrement of the material).

First Embodiment

Figure 1:
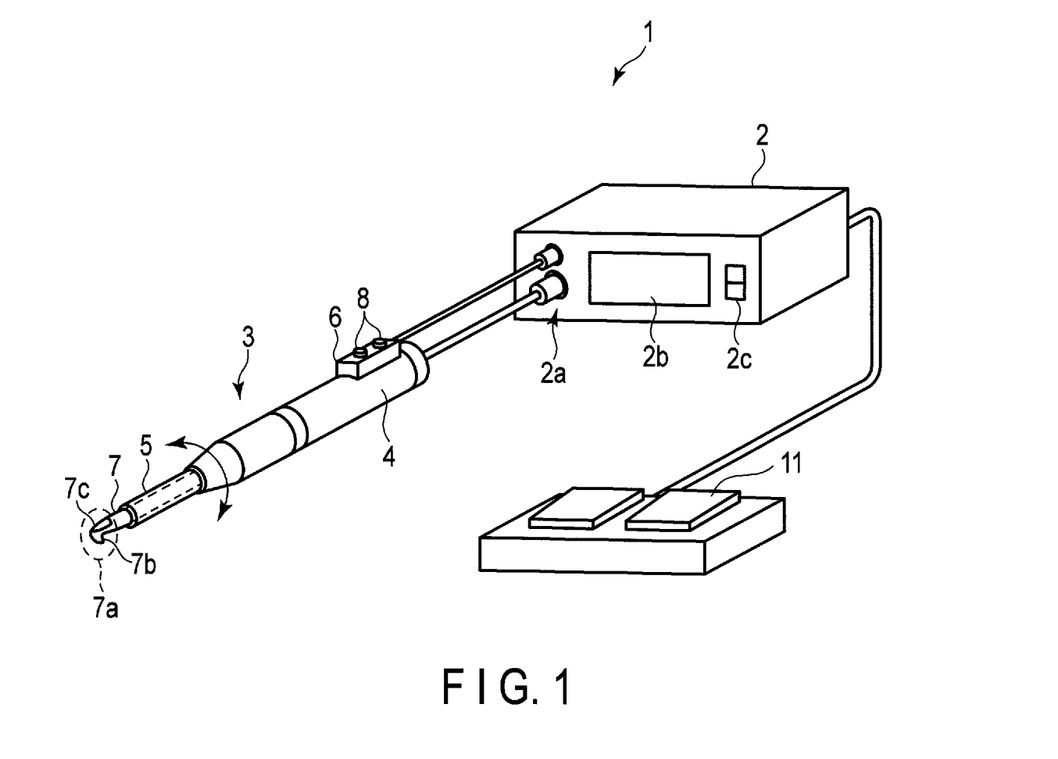
FIG. 1 is a view illustrating an example of an external appearance configuration of an ultrasonic treatment instrument according to a first embodiment.
Figure 2:
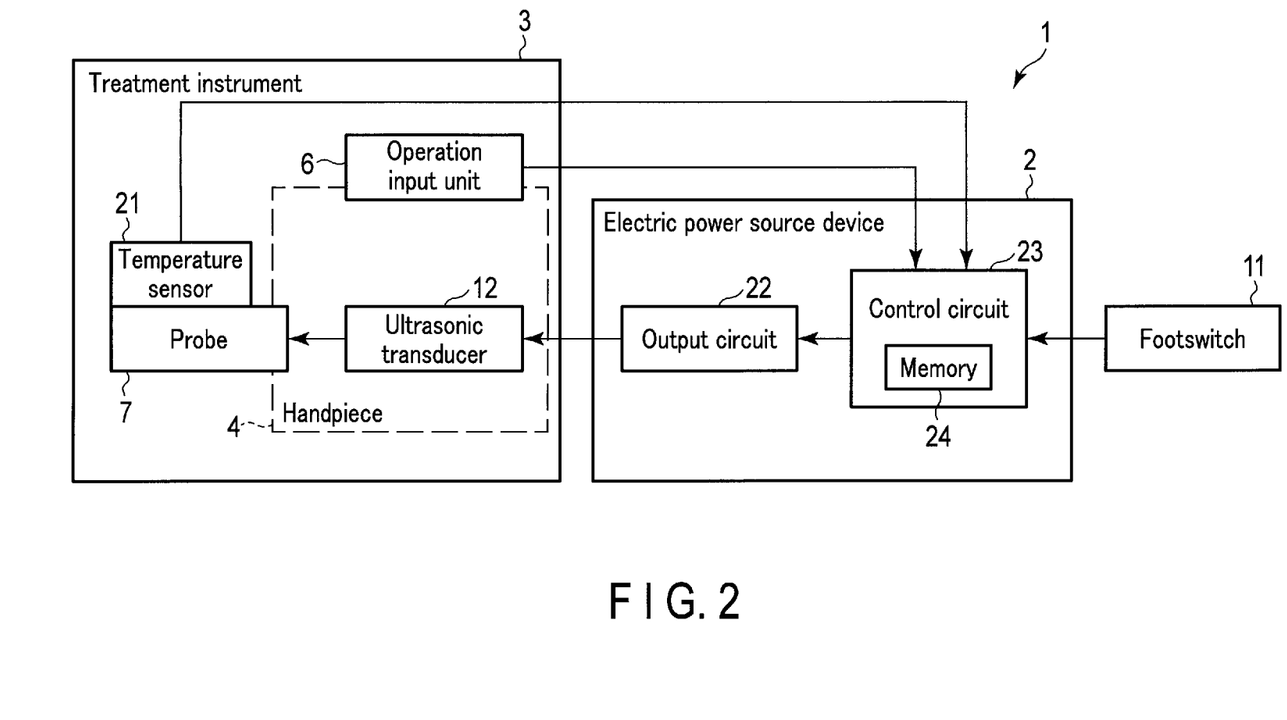
FIG. 2 is a block diagram illustrating a main configuration of the ultrasonic treatment instrument according to the first embodiment.

Referring to FIG. 1, an ultrasonic treatment instrument for articulations according to a first embodiment of the present invention will be described. FIG. 1 is a view illustrating an example of an external appearance configuration of the ultrasonic treatment instrument for articulations (hereinafter referred to as "ultrasonic treatment instrument") according to the first embodiment. FIG. 2 is a block diagram illustrating a main configuration of the ultrasonic treatment instrument. The present embodiment is a configuration example in which heat is generated by internal friction of the probe by incorporating a metallic material with a large damping factor into the above-described cartilage abrasion portion.

The ultrasonic treatment instrument 1 includes a treatment instrument 3 for performing, by ultrasonic vibration, an abrasion treatment or an opening-and-cutting treatment on a treated target part such as a living body tissue, a cartilage, a bone (subcartilaginous bone), etc.; an electric power source device 2 which supplies driving electric power to the treatment instrument 3; and a footswitch 11 having the same function as an operation input unit 6 (to be described later). Note that in the ultrasonic treatment instrument 1 of the present embodiment, a minimum system configuration for describing the gist of the technical features is illustrated, and it is assumed that structural parts, which are not illustrated but are generally used as an ultrasonic surgery system, are provided.

The treatment instrument 3 includes a cylindrical handpiece 4 which a surgeon holds; an elongated probe 7 which extends from one end of the handpiece 4; a sheath 5 formed in a manner to cover the periphery of the probe 7; an operation input unit 6 for issuing an instruction; and a temperature sensor 21 which measures the temperature of a cartilage abrasion portion 7c (to be described later) of the probe 7. The handpiece 4 is connected to the electric power source device 2 by a cable, and driving electric power is supplied or a control signal is communicated.

An ultrasonic transducer 12 is provided in the inside of the handpiece 4. The ultrasonic transducer 12 is acoustically coupled to the probe 7 via a horn section (not shown) or the like. The ultrasonic transducer 12 is supplied with driving electric power from the electric power source device 2, and generates ultrasonic vibration. The generated ultrasonic vibration is propagated to the probe 7. The probe 7 is covered with the sheath 5 such that a distal portion, which serves as a treatment section 7a, is exposed. The treatment section 7a vibrates by the ultrasonic vibration which is propagated from the ultrasonic transducer 12.

The treatment section 7a includes a bone abrasion portion 7b for abrading a living body tissue or a bone, and the cartilage abrasion portion 7c for abrading a cartilage. As will be described later, ultrasonic vibration is propagated, and an abrasion treatment of a cartilage is performed in the state in which the cartilage abrasion portion 7c is heated, or an abrasion treatment of a bone (e.g. a subcartilaginous bone) is performed in the state in which the bone abrasion portion 7b vibrates.

The handpiece 4 is provided with the operation input unit 6 on the cable side of a side surface thereof, which serves as a grasping surface. As will be described later in this embodiment, since a surgeon re-grasps the handpiece 4 by making a half rotation of the handpiece 4, this operation input unit 6 is disposed at such a position that the operation input unit 6 does not interfere with the fingers or hands when the surgeon re-grasps the handpiece 4.

This operation input unit 6 includes a plurality of operation switches 8 for instructing the driving of the ultrasonic transducer 12. The operation switches 8 include not only a switch for an ON/OFF operation of driving electric power which is supplied to the ultrasonic transducer 12. The operation switches 8 also include a change-over switch (switching portion) for performing an operation of switching between a cartilage abrasion mode and a bone abrasion mode. In the cartilage abrasion mode, the amplitude of an ultrasonic wave in the treatment (to be described later) is changed, and heat due to a small amplitude (or low amplitude) is generated. In the bone abrasion mode, the treatment section is vibrated with a larger amplitude (higher amplitude) than in the cartilage abrasion mode. In the present embodiment, the footswitch 11 has the same function as the operation input unit 6.

The electric power source device 2 is composed of an output circuit 22 which supplies driving electric power to the ultrasonic transducer 12, and a control circuit 23 which controls the output circuit 22.

The output circuit 22 is electrically connected to the ultrasonic transducer 12 in the handpiece 4 over a cable or the like, and supplies driving electric power for driving the ultrasonic transducer 12.

The control circuit 23 is composed of a processing circuit which includes therein a memory 24 and has an arithmetic processing function. The control circuit 23 controls the driving electric power which is output from the output circuit 22, in accordance with an instruction (ON/OFF instruction, or ultrasonic amplitude select instruction, etc.) which is input from the operation input unit 6 or footswitch 11, and a detection signal from the temperature sensor 21. The control circuit 23 controls, based on the detection signal of the temperature sensor 21, the driving electric power which is supplied to the cartilage abrasion portion 7c, such that the cartilage abrasion portion 7c has temperatures in the above-described temperature range (the range of 45° C. to 220° C., more preferably 120° C. to 160° C.) that is suitable for treatment.

Note that when temperature control for the cartilage abrasion mode 7c is executed, this can be realized even with a configuration without the temperature sensor 21. In this case, for example, a pushing weight is set at a fixed value, and such amplitude values as to set the temperature of the cartilage at a specified temperature in the range of 45° C. to 220° C., more preferably 120° C. to 160° C., are calculated by a plurality of times of actual measurement. An averaged amplitude value is prestored as a control parameter in the memory 24 of the control circuit 23. At the time of use, the control circuit 23 may read out from the memory 24 the control parameter which realizes the required set temperature, and may control the value of driving electric power of the output circuit 22 such that the ultrasonic transducer 12 vibrates with an amplitude value based on this control parameter.

Figure 3:
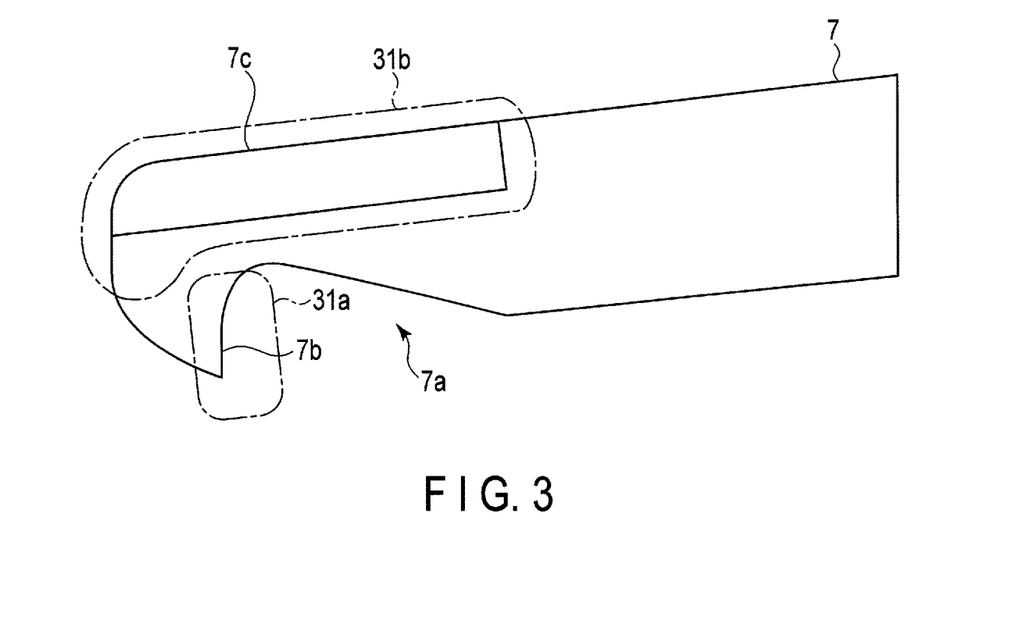
FIG. 3 is a view illustrating a conceptual external appearance configuration of a treatment section provided in a probe in the first embodiment.

FIG. 3 is a view illustrating a conceptual external appearance configuration of the treatment section 7a provided in the probe 7 in the present embodiment. The treatment section 7a is provided on the distal side of the probe 7. In FIG. 3, the bone abrasion portion 7b having a projecting hook shape is provided on a lower part of the treatment section 7a. The cartilage abrasion portion 7c, which is formed of a smooth surface without irregularities, i.e. a smooth planar surface or a smooth curved surface, is provided on an upper part of the treatment section 7a on the opposite side to the bone abrasion portion 7b.

Normally, the treatment section 7a of the probe 7 in the ultrasonic vibration treatment instrument abrades a living body tissue or bone that is a treated target part so as to crush the living body tissue or bone by mechanical abrasion (so-called "hammering effect" or "hammering function") for abrasion by beating and crushing with ultrasonic vibration. Thus, the treatment section 7a needs to have a higher rigidity than the bone of the treated target, and to have durability to vibration. On the other hand, since heat generation has not been regarded as a merit in abrasion, the treatment section 7a is formed by using a metallic material which hardly generates heat even if vibration is applied, i.e. a material with less damping, such as titanium or a titanium alloy.

The cartilage abrasion portion 7c in the present embodiment is formed by using a material with large damping, which easily generates heat, such as a stainless alloy or iron, in order to raise the temperature of the cartilage of the treated target part up to a temperature for dissolution by ultrasonic vibration. From the standpoint of sterilization treatment and resistance to corrosion, a stainless alloy is preferable to iron. In FIG. 3, for example, the bone abrasion portion 7b, which is formed of the titanium alloy, and the cartilage abrasion portion 7c, which is formed of the stainless alloy, are integrally bonded. In this configuration, if ultrasonic vibration is applied to the cartilage abrasion portion 7c, heat is generated by internal friction, and the cartilage abrasion portion 7c is more easily heated than the bone abrasion portion 7b.

As illustrated in FIG. 3, the distal side of the probe 7 includes a mechanical abrasion region 31a centering on the hook-shaped projection which beats and abrades the treated target part by ultrasonic vibration, and a dissolutive abrasion region 31b which abrades the treated target part by dissolution with the heat generated by ultrasonic vibration over a range from the distal end to the upper smooth part of the cartilage abrasion portion 7c. By pushing these regions on the treated target, abrasion is performed by these regions.

The bone abrasion portion 7b and cartilage abrasion portion 7c can be integrally bonded by using a bonding method such as shrinkage fit, welding, thermocompression bonding, screwing, or insert formation. A description will now be given of an abrasion treatment by the ultrasonic vibration treatment instrument including the probe 7 that is provided with the thus formed treatment section 7a.

To begin with, in order to form a port for an arthroscope by cutting and opening a living body tissue, the surgeon operates the operation input unit 6 of the handpiece 4 or the footswitch 11, drives the ultrasonic transducer 12, causes the probe 7 to generate ultrasonic vibration, and pushes the bone abrasion portion 7b of the treatment section 7a on the living body tissue of the treated target. The bone abrasion portion 7b abrades the living body tissue by mechanical abrasion of ultrasonic vibration, and cuts and opens the living body tissue until the cartilage (degenerated cartilage) is exposed.

After the cartilage is exposed, the surgeon makes a half rotation of the handpiece 4 around the longitudinal axis of the probe 7 as indicated by an arrow in FIG. 1, and re-grasps the handpiece 4, thus reversely rotating the probe. Then, the surgeon applies the cartilage abrasion portion 7c, which is heated by ultrasonic vibration, to the cartilage of the treated target. At this time, the temperature of the cartilage, with which the cartilage abrasion portion 7c is put in contact, rises to about 120° C. to 160° C. as described above, abrasion is performed by dissolution, and a bone under the cartilage is exposed. In addition, when the bone is exposed, the surgeon re-grasps once again the handpiece 4 so as to make a half rotation of the handpiece 4 around the longitudinal axis of the probe 7, causes the bone abrasion portion 7b to generate ultrasonic vibration, applies the bone abrasion portion 7b to the bone of the treated target, and abrades the bone by mechanical abrasion by ultrasonic vibration.

In the present embodiment, since the handpiece 4 and probe 7 are configured to be fixed, the surgeon makes a half rotation of the handpiece 4 and re-grasps the handpiece 4 when switching the bone abrasion portion 7b and cartilage abrasion portion 7c. In comparison with this fixed configuration, if a rotary mechanism is provided between the handpiece 4 and probe 7 and the probe 7 is rotatable relative to the handpiece 4, the surgeon can switch the directions of the bone abrasion portion 7b and cartilage abrasion portion 7c by rotating the probe 7 while holding the handpiece 4.

As described above, in the present embodiment, the metallic material with characteristics of damping capacity, which converts vibration energy to heat energy, is used as apart of the treatment section 7a of the probe 7 which performs mechanical abrasion by ultrasonic vibration, thereby constituting the cartilage abrasion portion 7c which abrades the cartilage by dissolutive abrasion.

According to the probe 7 of the present embodiment, when the treated target has a structure in which a cartilage is stacked on a subcartilaginous bone, the subcartilaginous bone is hardly abraded by dissolutive abrasion, and the cartilage abrasion portion 7c has the smooth planar surface or curved surface and has low efficiency of mechanical abrasion by ultrasonic vibration. Thus, the abrasion can be stopped after only the cartilage is abraded. Therefore, the probe 7 can easily cut and divide the living body tissue, cartilage and bone (e.g. subcartilaginous bone) with low invasion, by selectively using the mechanical abrasion by ultrasonic vibration of the bone abrasion portion 7b and the dissolutive abrasion by heat of the cartilage abrasion portion 7c in accordance with the treated target.

According to the present embodiment, the probe 7 can perform an abrasion treatment for all of a cartilage, a bone (subcartilaginous bone), a cancellous bone and a living body tissue. Moreover, the ultrasonic treatment instrument for articulations can be realized in which the probe 7 includes the treatment section which includes, in accordance with the parts of the probe which are applied to the treated target, both the bone abrasion portion 7b which abrades the living body tissue or bone of the treated target by the mechanical function by ultrasonic vibration, and the cartilage abrasion portion 7c which abrades the cartilage of the treated target by dissolution by generating heat by ultrasonic vibration.

Next, a first modification according to the first embodiment will be described.

Figure 4A:
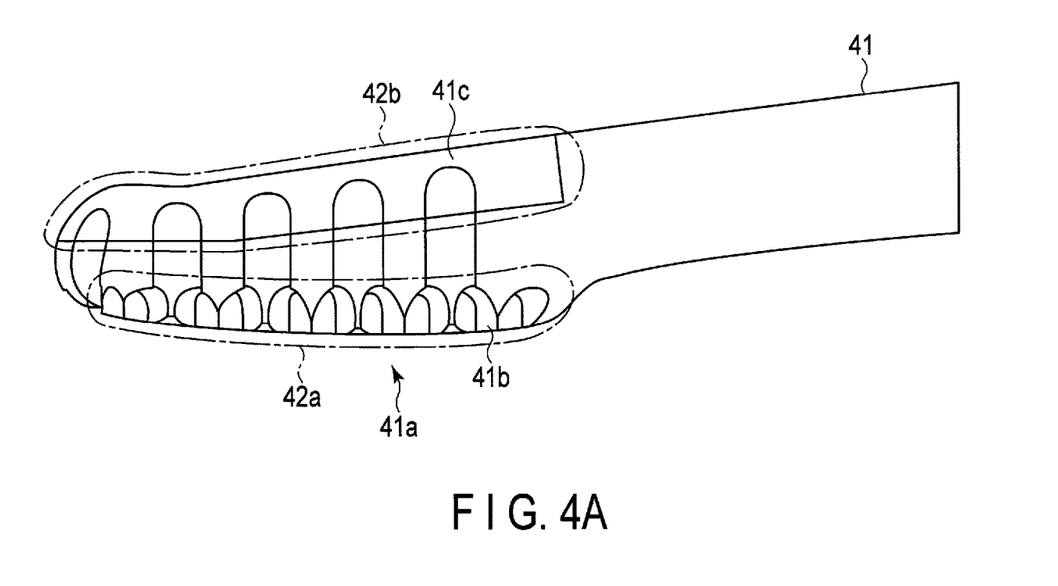
FIG. 4A is a view illustrating a conceptual external appearance configuration of a treatment section, as viewed from a lateral surface side, which is provided in a probe in a first modification of the first embodiment.
Figure 4B:
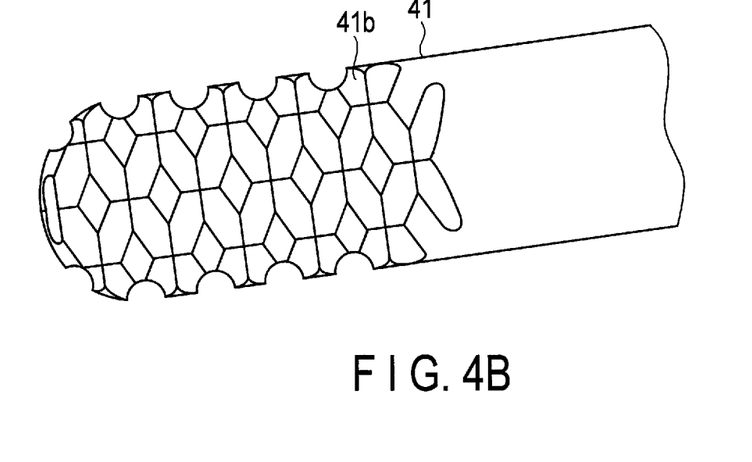
FIG. 4B is a view illustrating a conceptual external appearance configuration of the treatment section, as viewed from a front surface side, which is provided in the probe in the first modification of the first embodiment.

FIG. 4A illustrates a conceptual external appearance configuration of a treatment section 41a, as viewed from a lateral surface side, which is provided in a probe 41 which is applicable to the first embodiment. FIG. 4B illustrates a conceptual external appearance configuration of the treatment section, as viewed from a front surface side. This first modification is a configuration in which the hook shape of the bone abrasion portion 7b provided in the treatment section 7a of the above-described probe 7 is changed to a cross-hatching shape.

In the same manner as described above, the treatment section 41a is integrally formed of at least two dissimilar metals with different dampings. In the treatment section 41a, a bone abrasion portion 41b formed of the above-described titanium alloy and a cartilage abrasion portion 41c formed of the stainless alloy are integrally formed.

The cartilage abrasion portion 41c is formed of a smooth planar surface or curved surface, and ultrasonic vibration is applied as described above, and heat is generated by internal friction. The cartilage abrasion portion 41c is heated such that the cartilage, with which the cartilage abrasion portion 41c is put in contact, rises up to the above-described range of about 120° C. to 160° C.

In addition, when the bone abrasion portion 41b is viewed from the front surface side, a contact portion is formed in a cross-hatching mesh-like shape. Groove-like portions are formed between the meshes. In the mesh-like shape, a plurality of projection portions (edges), which cross in line shapes, are present, and semicircular grooves (edges) are formed on substantially the entire periphery of the side surfaces.

As illustrated in FIG. 4A and FIG. 4B, the distal side of the probe 41 includes a mechanical abrasion region 42a centering on the mesh-like contact portion which beats and abrades the treated target part by ultrasonic vibration, and a dissolutive abrasion region 42b which abrades the treated target part by dissolution over a range from the probe distal front face to the upper smooth part of the cartilage abrasion portion 41c.

According to the above first modification, since the cross-hatching portion comes in contact with the treated target, the bone abrasion portion 41b, compared to the hook-shaped bone abrasion portion 7b, has a larger contact area of existing projections (edges) and a higher efficiency of abrasion. Moreover, the same advantageous effects as with the ultrasonic treatment instrument according to the above-described first embodiment can be obtained.

Next, a second modification according to the first embodiment will be described.

Figure 5:
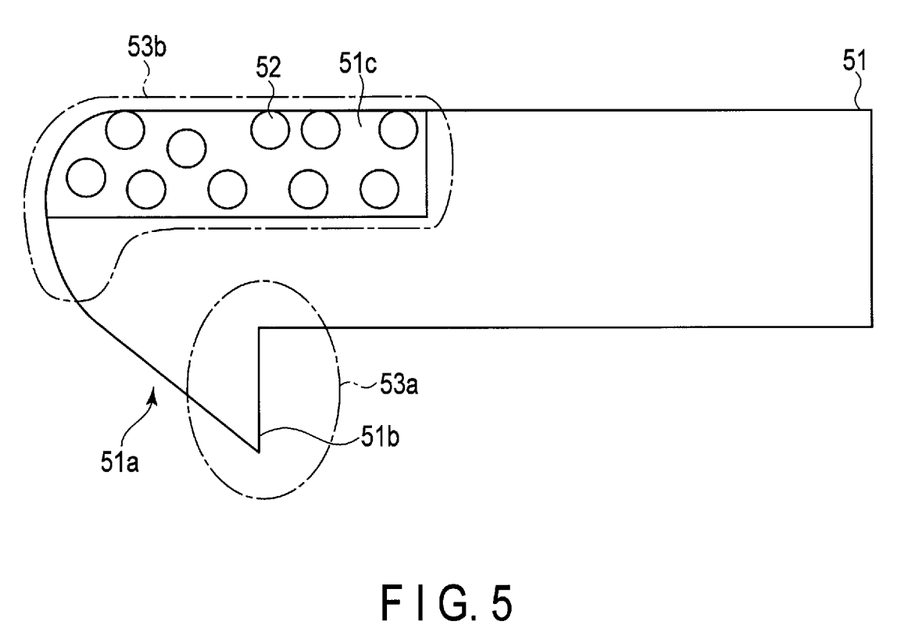
FIG. 5 is a view illustrating a conceptual external appearance configuration of a treatment section, as viewed from a lateral surface side, which is provided in a probe in a second modification of the first embodiment.

FIG. 5 illustrates a conceptual configuration of a treatment section 51a, as viewed from a lateral surface side, which is provided in a probe 51 that is applicable to the first embodiment. This second modification is a modified configuration of the cartilage abrasion portion 7c provided in the treatment section 7a of the above-described probe 7.

In the treatment section 51a, a bone abrasion portion 51b formed of the above-described titanium alloy and a cartilage abrasion portion 51c are integrally formed. As illustrated in FIG. 5, the distal side of the probe 51 includes a mechanical abrasion region 53a centering on a hook-shaped projection which beats and abrades the treated target part by ultrasonic vibration, and a dissolutive abrasion region 53b which abrades the treated target part by dissolution with the heat by ultrasonic vibration over a range from the probe distal front face to the upper smooth part of the cartilage abrasion portion 51c.

In the cartilage abrasion portion 51c, as a dissimilar metal, a metal such as iron or a stainless alloy, which easily generates heat by the application of ultrasonic vibration, is buried in the titanium alloy in the form of small spherical bodies 52. An inclusion amount (quantity, or a size such as a diameter) of small spherical bodies 52, which are buried in the titanium alloy, is set by actually measuring the heat generation state of the cartilage abrasion portion 51c at a time when ultrasonic vibration is actually applied. Accordingly, the inclusion amount is properly set, based on the size, shape, heat generation temperature, etc. of the probe 51. In addition, the distribution (density) of buried small spherical bodies 52 may be uniform, or may be designed to become higher in a region which is to be particularly heated, than in other regions.

According to this second modification, in addition to the advantageous effects of the above-described first embodiment, the adjustment of the temperature range at the time of manufacture can easily be implemented by burying the cartilage abrasion portion 51c in an upper part of the probe 51 formed of the titanium alloy, by properly setting the number and size of small spherical bodies which are formed of a metal dissimilar to the titanium alloy.

Next, a third modification according to the first embodiment will be described.

Figure 6:
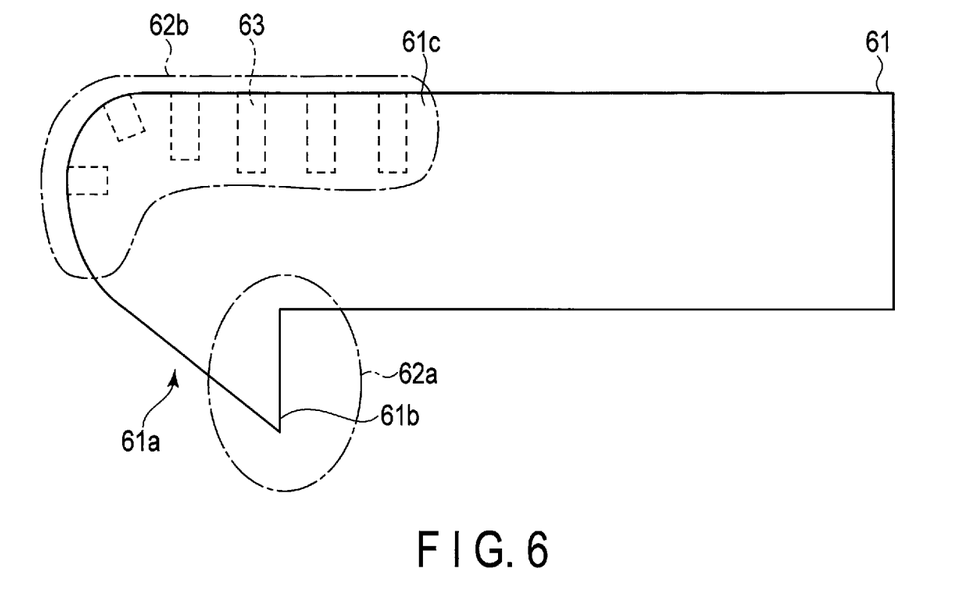
FIG. 6 is a view illustrating a conceptual external appearance configuration of a treatment section, as viewed from a lateral surface side, which is provided in a probe in a third modification of the first embodiment.

FIG. 6 illustrates a conceptual configuration of a treatment section 61a, as viewed from a lateral surface side, which is provided in a probe 61 that is applicable to the first embodiment. This third modification is a modified configuration of the cartilage abrasion portion 7c provided in the treatment section 7a of the above-described probe 7.

In the treatment section 61a, a bone abrasion portion 61b formed of the above-described titanium alloy and a cartilage abrasion portion 61c are integrally formed, the cartilage abrasion portion 61c being configured such that dissimilar-metal columns 63, which are formed of a dissimilar metal in cubic pillar shapes or columnar shapes, are buried in an upper part of the probe 61.

A plurality of fit-in holes are formed in an upper surface of the distal portion of the probe 61 which is formed of the titanium alloy. For example, a heat treatment is performed in the state in which the dissimilar-metal columns 63 formed of a stainless alloy are fitted in the fit-in holes, and the titanium alloy and stainless alloy are integrated. As illustrated in FIG. 6, the distal side of the probe 61 includes a mechanical abrasion region 62a centering on a hook-shaped projection which beats and abrades the treated target part by ultrasonic vibration, and a dissolutive abrasion region 62b which abrades the treated target part by dissolution with the heat by ultrasonic vibration over a range from the distal end to the upper smooth part of the cartilage abrasion portion 61c.

Besides, screws formed of iron or a stainless alloy may be substituted for the dissimilar-metal columns 63. Specifically, a plurality of screw holes are formed in the distal upper surface of the probe 61, and the screws are engaged in the screw holes. Further, the screw head portions may be cut off, and the cut parts may be subjected to a polishing and planarizing process. If the screw head portions have, for example, the shape of flat-head screws, and the screw head portions are configured to be flush with the distal upper surface of the probe 61 and do not protrude, the screw head portions may not necessarily be eliminated. Moreover, grooves for screw drivers on the screw head portions may not necessarily be eliminated.

According to the third modification, in addition to the advantageous effects of the above-described first embodiment, a dissimilar metal can be buried in a later process in the probe formed of the titanium alloy or the like, and the cartilage abrasion portion 61c can easily be fabricated. Furthermore, it is easy to bury the dissimilar metal, and the temperature of heat generated by ultrasonic vibration can easily be adjusted by adjusting the quantity and distribution of the buried dissimilar metal. Besides, the cartilage abrasion portion 61c can easily be formed by engaging the screws of the dissimilar metal into the screw holes formed in the distal upper surface of the probe, instead of fitting in the dissimilar-metal columns 63.

Next, a fourth modification according to the first embodiment will be described.

Figure 7:
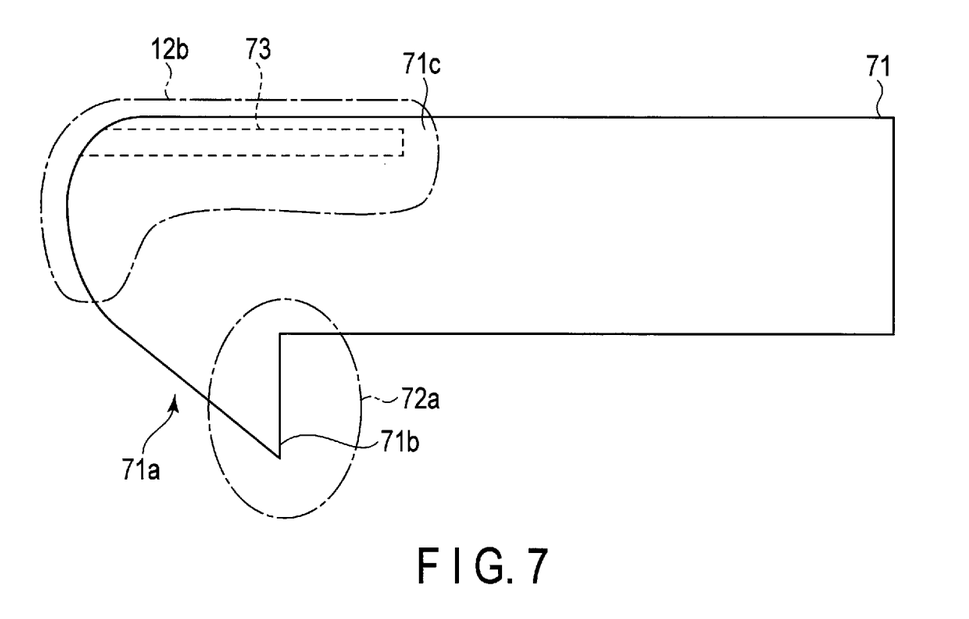
FIG. 7 is a view illustrating a conceptual external appearance configuration of a treatment section, as viewed from a lateral surface side, which is provided in a probe in a fourth modification of the first embodiment.

FIG. 7 illustrates a conceptual configuration of a treatment section 71a, as viewed from a lateral surface side, which is provided in a probe 71 that is applicable to the first embodiment. This fourth modification is a modified configuration of the cartilage abrasion portion 7c provided in the treatment section 7a of the above-described probe 7.

In the present embodiment, a fit-in hole is formed which extends in the longitudinal axial direction of the probe from the front surface of the distal portion of the probe 7 formed of the titanium alloy. This fit-in hole is formed in a track shape or a rectangular shape in radial cross section. A heat treatment is performed in the state in which a dissimilar-metal plate 73 formed of, for example, a stainless alloy, which has the same cross section as the plane shape of the fit-in hole, is tightly fitted in the fit-in hole, and the titanium alloy and stainless alloy are integrated. As illustrated in FIG. 7, the distal side of the probe 71 includes a mechanical abrasion region 72a centering on a hook-shaped projection which beats and abrades the treated target part by ultrasonic vibration, and a dissolutive abrasion region 72b which abrades the treated target part by dissolution with the heat by ultrasonic vibration over a range from the distal end to the upper smooth part of the cartilage abrasion portion 71c.

According to the fourth modification, in addition to the advantageous effects of the above-described first embodiment, a dissimilar metal can be buried in a later process in the probe formed of the titanium alloy or the like, and the cartilage abrasion portion 71c can easily be fabricated. Furthermore, it is easy to bury the dissimilar metal, and the temperature of heat generated by ultrasonic vibration can easily be adjusted by adjusting the size (cross-sectional area and length) of the buried dissimilar metal.

Second Embodiment

An ultrasonic treatment instrument for articulations according to a second embodiment of the present invention will be described. The above-described first embodiment illustrates the configuration example in which heat is generated by utilizing the damping capacity of the metallic material. The present second embodiment has a configuration in which heat is generated by utilizing residual stress. Residual stress is applied to the regions of the cartilage abrasion portion 7c and cartilage abrasion region 41c illustrated in FIG. 3, FIG. 4A and FIG. 4B.

Residual stress is applied in advance by a general method, for example, plastic deformation or hardening (heating and quick cooling) at the time of manufacture of the probe 7, and the residual stress can be generated by applying vibration. For example, by heating such as hardening in the manufacturing process, local expansion of a metallic material is generated. Although a region melted during the heating absorbs expansion, residual stress occurs by local quick cooling, compared to a slowly cooled region. Examples of the heating method include a contact with a heat source, high-frequency heating, irradiation of a laser, etc. Note that means such as plastic deformation, which is not shot peening, is preferable.

By forming the cartilage abrasion portion 7c, 41c having this residual stress, like the above-described first embodiment, the treated target part can be beaten and abraded by ultrasonic vibration by that part of the distal side of the probe 7, which centers on the hook-shaped projection of the mechanical abrasion region 31a. Moreover, the dissolutive abrasion region 31b can abrade the treated target part by dissolution with the heat generated by ultrasonic vibration over the range from the distal end to the upper smooth part of the cartilage abrasion portion 7c.

Third Embodiment

Figure 8:
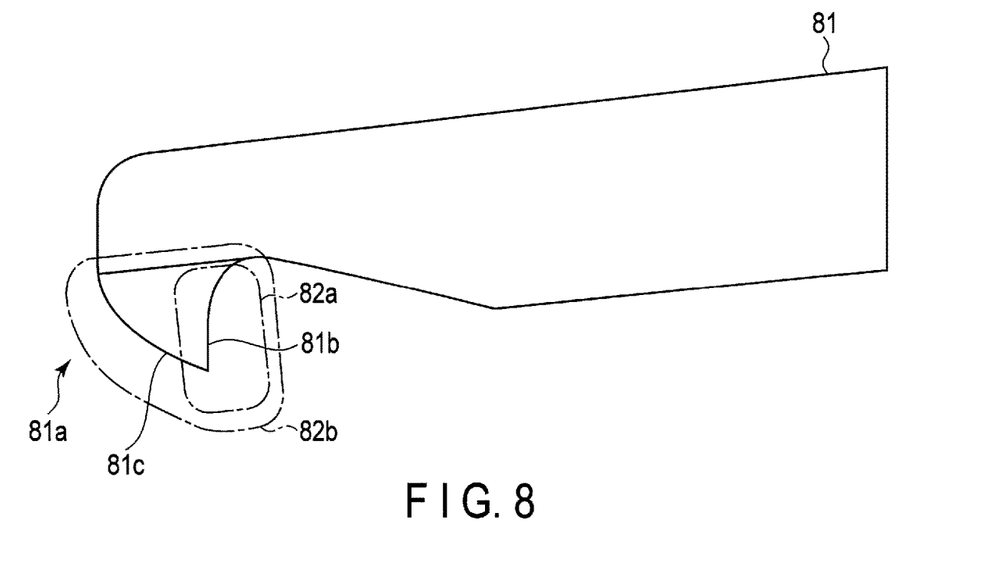
FIG. 8 is a view illustrating a conceptual external appearance configuration of a treatment section, as viewed from a lateral surface side, which is provided in a probe in an ultrasonic treatment instrument according to a third embodiment.

Referring to FIG. 8, an ultrasonic treatment instrument for articulations according to a third embodiment of the present invention will be described. FIG. 8 illustrates a conceptual configuration of a treatment section 81*a*, as viewed from a lateral surface side, which is provided in a probe 81 in the ultrasonic treatment instrument according to the third embodiment.

In the present embodiment, the apparatus configuration is the same as the above-described ultrasonic treatment instrument illustrated in FIG. 1. However, the ultrasonic transducer 12 illustrated in FIG. 2 is configured to output at least two different driving electric powers from the output circuit 22 such that the ultrasonic transducer 12 vibrates with at least two different amplitudes of ultrasonic vibration. In addition, the present embodiment has a configuration in which the cartilage abrasion portion and bone abrasion portion in the treatment section 81*a* of the probe 81 are provided at the same location. The other configuration is the same as in the ultrasonic treatment instrument of the first embodiment, and a description thereof is omitted. As illustrated in FIG. 8, the material, of which the bone abrasion portion 81*b* is formed, is changed from the titanium alloy to the stainless alloy, and a hook-shaped projection is formed. Since this projection is formed of the stainless alloy, the projection generates heat and functions as a cartilage abrasion portion 81*c* if ultrasonic vibration is applied to the projection. Here, in the treatment section 81*a* at the distal end of the probe 81, a mechanical abrasion region 82*a*, which abrades the treated target part by beating the treated target part by ultrasonic vibration, and a dissolutive abrasion region 82*b*, which abrades the treated target part by dissolution with the heat generated by ultrasonic vibration, overlap each other.

Switching between the mechanical abrasion region 82*a* and dissolutive abrasion region 82*b* in the same region of the treatment section 81*a* can be realized by a difference in amplitude of ultrasonic vibration. Specifically, an amplitude of a certain degree of magnitude is necessary in order to generate a hammering function which beats and abrades the treated target part by ultrasonic vibration. On the other hand, a heat generation function for dissolution occurs by driving with a smaller amplitude than in the bone abrasion.

Accordingly, switching is possible by using two abrasion modes, i.e., the bone abrasion mode which vibrates the treatment section 81*a*, and the cartilage abrasion mode which generates heat. In the bone abrasion mode, the treatment section 81*a* is caused to vibrate with a high amplitude (first amplitude) by using a first ultrasonic vibration with which, although heat is generated, the function of mechanical abrasion is greater. In the cartilage abrasion mode, heat is generated with a low amplitude (second amplitude) by using a second ultrasonic vibration with which, although heat for dissolution can be generated, an amplitude enough to cause the function of mechanical abrasion is not generated. The switching operation is executed by the operation switch 8 of the operation input unit 6, or by the footswitch 11. The switching of the ultrasonic vibration can be executed by operating the operation switch 8 of the operation input unit 6 provided on the handpiece 4 illustrated in FIG. 1.

Note that the cartilage abrasion mode and bone abrasion mode, in which the amplitude of the ultrasonic vibration is changed, are also applicable to the above-described first embodiment and first to fourth modifications.

Besides, in the ultrasonic treatment instrument of the present embodiment, since the mechanical abrasion region 82*a* and dissolutive abrasion region 82*b* are switched in the same region of the treatment section 81*a*, there is no need to re-grasp the handpiece 4 each time by making a half rotation of the handpiece 4, and the load of a surgical operation on the surgeon is reduced.

Next, a modification according to the third embodiment will be described.

Figure 9:
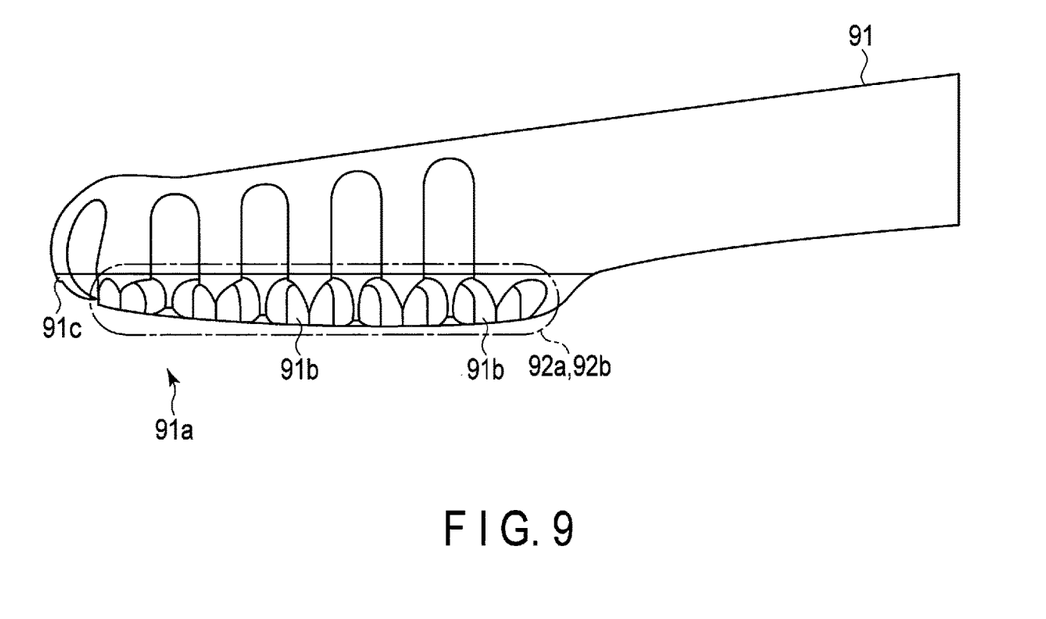
FIG. 9 is a view illustrating a conceptual external appearance configuration of a treatment section, as viewed from a lateral surface side, which is provided in a probe in a modification of the third embodiment.

FIG. 9 illustrates a conceptual configuration of a treatment section 91*a*, as viewed from a lateral surface side, which is provided in a probe 91 that is applicable to the third embodiment. The cross-hatching shape of the treatment section 91*a*, as viewed from the front surface side, is the same as the configuration illustrated in FIG. 4B. This modification is a configuration in which the hook shape of the bone abrasion portion 81*b* (cartilage abrasion portion 81*c*) provided in the treatment section 81*a* of the above-described probe 81 is changed to a cross-hatching shape. The other configuration is the same as the configuration in the second embodiment.

This modification has the same cross-hatching shape as the bone abrasion portion 41*b* of probe 91 of the treatment section 41*a* of the above-described first modification according to the first embodiment. However, as the dissimilar metal, for example, a stainless alloy is used in place of the titanium alloy, and the dissimilar metal is integrally formed in the main body of the probe 91 of the titanium alloy.

In the present modification, as illustrated in FIG. 9, the probe 91 is configured such that a mechanical abrasion region 92*a*, which abrades the treated target part by beating the treated target part by ultrasonic vibration, and a dissolutive abrasion region 92*b*, which abrades the treated target part by dissolution with the heat generated by ultrasonic vibration, are set in the same region centering on the hook-shaped projection of the treatment section 91*a*, and the mechanical abrasion and dissolutive abrasion are switched by changing the amplitude of ultrasonic vibration.

According to the above modification, since the cross-hatching portion comes in contact with the treated target, the bone abrasion portion 91*b* and cartilage abrasion portion 91*c*, compared to the hook-shaped bone abrasion portion 81*b*, have a larger contact area and a higher efficiency of abrasion. Moreover, the same advantageous effects as with the ultrasonic treatment instrument according to the above-described third embodiment can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An ultrasonic treatment instrument for articulations, comprising:
   an ultrasonic vibration generator configured to generate ultrasonic vibration;
   an ultrasonic probe configured to transmit the ultrasonic vibration; and
   a treatment section provided at a distal end of the ultrasonic probe and configured to perform a desired treatment on a treated target part,
   the treatment section comprising:
   a bone abrasion portion configured to come in contact with a living body tissue or a bone of the treated target part by a surface having an edge, and to configured to mechanically abrade the living body tissue or the bone by beating the living body tissue or the bone by the transmission of the ultrasonic vibration; and a cartilage abrasion portion provided at a different position from, or at an identical overlapping position to, a position of the bone abrasion portion, configured to come in contact with a cartilage of the treated target part, and configured to generate heat by the transmission of the ultrasonic vibration and to dissolutively abrade the cartilage.

2. The ultrasonic treatment instrument for articulations of claim 1, wherein the cartilage abrasion portion of the treatment section is formed of a member having a damping factor different from a damping factor of the bone abrasion portion.

3. The ultrasonic treatment instrument for articulations of claim 1, wherein the cartilage abrasion portion has a greater residual stress than the bone abrasion portion, the residual stress being given at a time of manufacture.

4. The ultrasonic treatment instrument for articulations of claim 1, wherein a temperature of the heat, which the cartilage abrasion portion generates by the transmission of the ultrasonic vibration, is in a range of 45° C. to 220° C.

5. The ultrasonic treatment instrument for articulations of claim 1, wherein the cartilage abrasion portion is formed by incorporating a member, which has a spherical shape, a columnar shape or a plate shape and has a different damping factor from a damping factor of the bone abrasion portion, into a member having a damping factor identical to the damping factor of the bone abrasion portion.

6. The ultrasonic treatment instrument for articulations of claim 1, wherein the cartilage abrasion portion and the bone abrasion portion are formed of dissimilar metals.

7. The ultrasonic treatment instrument for articulations of claim 1, wherein when the cartilage abrasion portion is formed at the different position from the position of the bone abrasion portion, the cartilage abrasion portion is formed to have a smooth surface.

8. The ultrasonic treatment instrument for articulations of claim 1, wherein the ultrasonic vibration generator is configured to generate a first ultrasonic vibration of a first amplitude, and a second ultrasonic vibration of a second amplitude which is less than the first amplitude, and the ultrasonic treatment instrument for articulations comprises a switching portion capable of effecting switching between a bone abrasion mode in which the treatment section is caused to vibrate by using the first ultrasonic vibration and a function of the mechanically abrading the bone is generated, and a cartilage abrasion mode in which the treatment section is caused to vibrate by using the second ultrasonic vibration and a function of the dissolutively abrading the cartilage is generated.

9. A treatment method of an ultrasonic treatment instrument for articulations, the treatment method being a method of abrading a treated target part by the ultrasonic treatment instrument for articulations of claim 1, the treatment method comprising:

generating ultrasonic vibration by the ultrasonic vibration generator, and transmitting the ultrasonic vibration to the ultrasonic probe;

causing the bone abrasion portion, which the treatment section provided at the distal end of the ultrasonic probe includes, to come in contact with the living body, tissue or the bone of the treated target part by the surface having the edge, and causing the bone abrasion portion to mechanically abrade the living body tissue or the bone by heating the living body tissue or the bone by the transmission of the ultrasonic vibration; and causing the cartilage abrasion portion, which the treatment section provided at the distal end of the ultrasonic probe includes and which is provided at a different position from, or at an identical overlapping position to, a position of the bone abrasion portion, to come in contact with the cartilage of the treated target part, and causing the cartilage abrasion portion to generate heat by the transmission of the ultrasonic vibration and to dissolutively abrade the cartilage.

* * * * *